United States Patent [19]

Diaz-Ramos

[11] Patent Number: 4,850,374

[45] Date of Patent: Jul. 25, 1989

[54] BLOOD SAMPLER WITH RETRACTABLE NEEDLE

[75] Inventor: Nydia Diaz-Ramos, Rio Piedras, P.R.

[73] Assignee: Commonwealth of Puerto Rico, San Juan, P.R.

[21] Appl. No.: 100,415

[22] Filed: Sep. 24, 1987

[51] Int. Cl.$^4$ .............................................. A61B 5/00
[52] U.S. Cl. .................................... 128/763; 128/770; 604/198
[58] Field of Search ................... 128/763, 764, 770; 604/52, 187, 272, 403, 412, 414, 415, 192, 194, 198

[56] References Cited

U.S. PATENT DOCUMENTS

| | | | |
|---|---|---|---|
| 3,656,472 | 4/1972 | Ben Moura | 128/763 |
| 4,398,544 | 8/1983 | Nugent et al. | 128/763 |
| 4,592,744 | 6/1986 | Jagger et al. | 128/763 |
| 4,643,199 | 2/1987 | Jennings et al. | 128/763 |

FOREIGN PATENT DOCUMENTS 2147824  3/1973  Fed. Rep. of Germany ...... 128/764

Primary Examiner—Max Hindenburg
Attorney, Agent, or Firm—Scrivener and Clarke

[57] ABSTRACT

A blood sampler of the type employing a double ended hollow needle, one end to be inserted into a vein and the other end to receive thereover a puncturable cover of an evacuated receptacle; the needle is rigidly secured to a slider which is slidable in a barrel having one end through which the needle may be extended out of or fully retracted into the barrel, and a second end through which the evacuated receptacle can be inserted for engagement with the other end of the needle after the latter has been moved and releasably locked in its extended position. A cap is provided to close the one end of the barrel when the needle is fully retracted thereinto.

13 Claims, 1 Drawing Sheet

BLOOD SAMPLER WITH RETRACTABLE NEEDLE

This invention relates to blood samplers and more particularly to blood samplers especially designed to protect an operator from being inadvertently pricked by the needle of the sampler or otherwise subjected to the blood being sampled upon completion of a blood withdrawal operation.

The present invention is concerned with that type of blood sampler wherein one end of a double ended hollow needle is inserted into a vein and the second end is adapted to receive thereover a puncturable cover of an evacuated receptacle. The second end of the needle has a rubber sleeve thereover which operates as a valve and is pushed down over the second end of the needle as the puncturable cover of the evacuated container is pushed onto the needle. As soon as the second end of the needle emerges on the other side of the cover inside the receptacle, the vacuum therein instantly draws a sample of blood into the receptacle. An advantage of this arrangement is that with the first end of the needle still inserted into the vein, an operator can collect a number of samples for different types of blood tests by merely inserting in succession a number of receptacles over the second end of the needle. The described system of blood sampling is well-known and the system, as so far described, forms no part of the invention.

A problem with the blood sampling system as just described is that when the first end of the needle is withdrawn from the vein the end remains exposed and it can be a source of great danger to the operator or to anyone who might be pricked or scratched by the exposed end of the needle. Prior to the present invention the only solution had been simply to drop the needle and its holder through a slot in the upper end of a trash receptacle.

The broad object of the present invention is to lessen the danger of being infected by an exposed blood sampling needle by providing a barrel into which the needle is normally housed and from which the needle can be extended in readiness for use. The invention provides means for releasably locking the needle in its extended position and then retracting the needle into the barrel preferably while it is still in the patient's vein until the needle is eventually withdrawn entirely into the barrel as it is withdrawn from the patient's vein.

The invention will now be described in conjunction with the accompanying drawings wherein.

Figure 5:
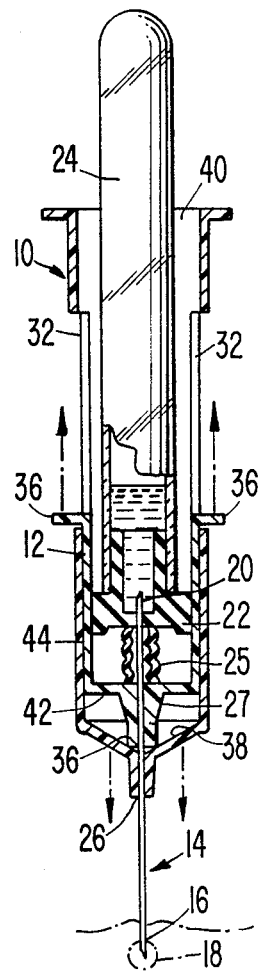
FIG. 5 is a vertical cross-sectional view showing the needle and evacuated receptacle in their positions of use when withdrawing a blood sample.
Figure 6:
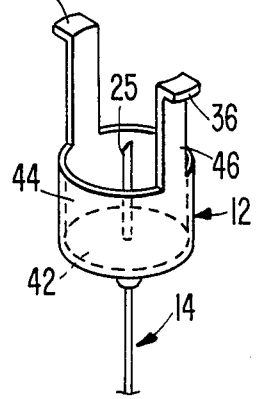
FIG. 6 is a perspective view of the slider which holds the double ended needle.

Referring now to the drawings the numeral 10 is directed to a barrel which slideably receives a slider 12 more clearly seen in FIG. 6. The slider rigidly supports intermediate it ends and co-axially in said barrel a hollow, double ended needle 14 whose first end 16 is adapted to be inserted into a patient's vein 18, as shown in FIG. 5, and whose second end 20 is adapted to receive thereover, in a known manner, a puncturable cover or stopper 22 of an evacuated receptacle 24. A source of such receptacles is Vacutainer Systems, Rutherford, N.J.

Though the needle 14 is shown as being molded into the slider itself, in actual practice a short sleeve of plastic is usually rigidly molded to the needle. The plastic sleeve is threaded and is screwed into a threaded bore in an axial projection corresponding to the projection 27 on the lower end of the slider 12. How the needle is rigidly fixed to the slider forms no part of the present invention. Covering the second end 20 of the needle is a rubber sleeve 25 which serves as a valve to prevent blood from issuing through the needle as soon as it is inserted into a vein. As the end 20 of the needle punctures the cap 22, the sleeve is moved clear of the open end by the cap 22 as should be clear in FIG. 5. This too is a feature entirely separate from the present invention.

Figure 1:
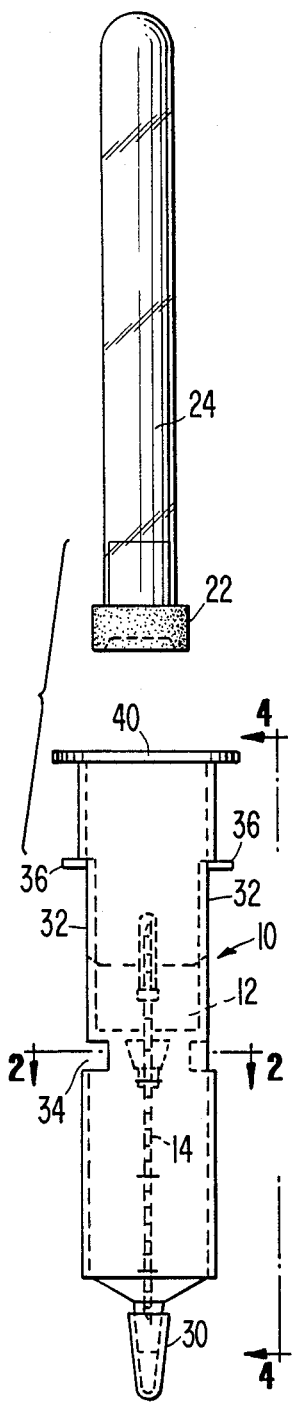
FIG. 1 is an elevational view of a barrel showing the needle withdrawn into the barrel and an evacuated receptacle poised over the barrel.
Figure 2:
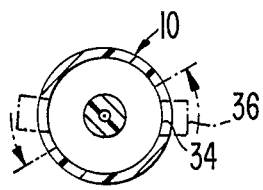
FIG. 2 is a horizontal cross-sectional view taken substantially on the line 2—2 of FIG. 1.
Figure 3:
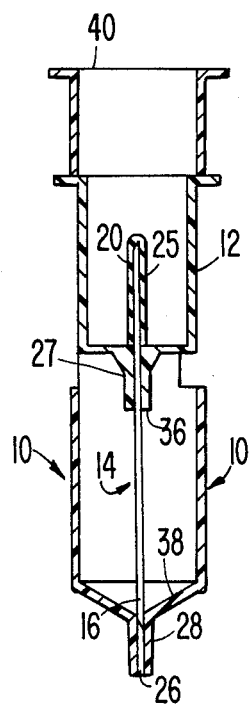
FIG. 3 is a vertical cross-sectional view of the invention showing the double ended needle in its retracted position.
Figure 4:
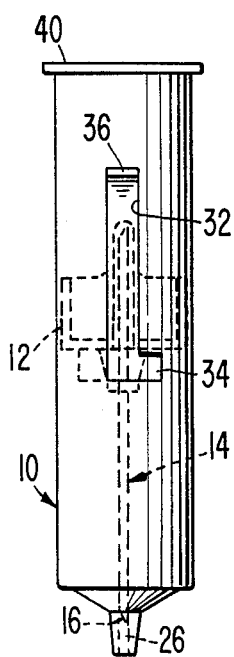
FIG. 4 is a vertical elevational view looking in the direction of 4—4 of FIG. 1.

The barrel 10 has a restricted opening 26 at its end 28 through which the first end 16 of the needle 14 may be extended when the slider 12 is moved to a first position proximate said end as shown in FIG. 5. The barrel has a length to permit the needle 14 to be entirely withdrawn into the barrel when the slider is moved to a second position remote from the end 28 as best shown in FIG. 3. When the needle is in its withdrawn position the opening 24 is closed by a cap 30 as shown in FIG. 2. Preferably, the lower end 28 of the barrel is tapered and the cap 30 is complementarily tapered for sealing reception over the opening 26.

Manually operable means are provided for moving the slider between its first and second positions and means are also provided for releasably locking the slider in its first position. Though the manually operable means may vary over a wide range, the means illustrated comprises a pair of diametrically opposed vertical slots 32 extending longitudinally through the wall of the barrel 10. The slots terminate in lateral recesses 34 at the ends of the slots proximate the opening 26 and the slider 12 includes parts 36 which extend laterally through the slots 32 and are engageably by the fingers of an operator to move the slider between its first and second positions, the laterally extending parts 36 being movable, by slight rotation thereof as shown in FIG. 2, into the recesses 34 to releasably lock the needle in its extended position after the slider has been moved to its first position.

The projection 27 of the slider, or it may the lower end of a screw threaded sleeve molded to the needle, has a lower annular edge 36 and the lower end of the barrel has a sloping inner surface 38. The edge 36 and surface 38 define interengaging stop means to limit the extension of the needle when the slider is moved to its first position as should be clear in FIG. 5. The releasable locking means, of whatever form, is operable to retain the stop means in interengagement after the slider has been moved to its first position, and to prevent retraction of the needle and slider as the first end 16 of the needle is inserted into a vein.

It will be seen that the end 40 of the barrel opposite the restricted opening 26 is open and of a size to permit the insertion of the evacuated receptacle 24 into the barrel for the puncturing of its cover 22 by the second end 20 of the needle after the slider has been moved to and locked in its first position of FIG. 5.

As can be best seen in FIG. 6, the slider 12 is a cup-shaped member having a bottom wall 42 and a side wall 44 whose outer diameter is complementary to the inner diameter of the barrel. The inner diameter of the wall 44 is complementary of the puncturable cover 22 of the receptacle 24 as should be clear in FIG. 5. The bottom wall 42 rigidly supports the needle intermediate its ends as described above.

It will be apparent to those skilled in this art that the releasable locking means may comprise interengaging ratchet like-teeth on the arms 46 carrying the projections 36 and integral with the upper edge of the side wall 44 of the slider as shown in FIG. 6. When the slider is moved to its first position, the teeth snap over each other to prevent reverse movement of the slider and needle as the latter is inserted into the vein. When the blood sampling is complete, the operator squeezes the projection 36 towards each other until the teeth unmesh whereupon the slider and needle are moved to the position of FIG. 3.

In the arrangement shown and described, the operator merely turns the projections 36 slightly in the opposite direction until they align with the slots 32 whereupon the slider and needle are withdrawn to the position of FIG. 3.

After the samples have been obtained in the receptacles the operator may remove the needle from the vein, release the locking means, and retract the needle wholly within the barrel. Alternatively, the needle may be retained in the vein, the locking means released and the barrel moved carefully in the direction of the lower end 16 of the needle, the operator retaining the needle stationary by engaging the projections 36 with her fingers. As the barrel approaches the patient, the needle is simultaneously withdrawn from the patient and pulled into the barrel. Regardless of what procedure is followed, as soon as the needle is withdrawn into the barrel the cover 30, which may have a threaded connection with the lower end 28 of the barrel, is replaced over the opening 26 and the entire assembly is discarded. It will be apparent in FIG. 3 that the projections 36 engage the upper ends of the slots 32 to prevent accidental dislodgement of the slider and needle from the barrel.

It should be understood, of course, that each assembly prior to use, is stored in an hermetically sealed, anti-septic container (not shown) in accordance with sound medical practice.

It will be apparent that the invention is susceptable of a variety of modifications and changes without, however, departing from the scope and spirit of the appended claims.

What is claimed is:

1. In a blood sampler of the type comprising a double ended hollow needle having a first end which is adapted to be inserted into a vein and a second end which is adapted to receive thereover a puncturable cover of an evacuated receptacle, the invention comprising a barrel having inner and outer ends, a slider slideably received in the barrel for movement therein only between said inner and outer ends, said slider rigidly supporting intermediate its end and co-axially in said barrel said double ended needle, said barrel having a restricted opening at its inner end through which the first end of said needle may be extended when said slider is moved to a first position within said barrel proximate said inner end, said barrel having a length to permit said needle to be entirely withdrawn into said barrel when said slider is moved to a second position remote from said inner end, and manually operable means for moving said slider between its first and second positions, said manually operable means having no part which at any time extends in an axial direction beyond the ends of said barrel.

2. In the blood sampler of claim 1, including a cap for closing said opening at the outer end of said barrel.

3. In the blood sampler of claim 2 wherein said outer end of said barrel containing said opening is tapered and said cap is complementarily tapered for sealing reception over said opening.

4. In the blood sampler of claim 1, wherein said manually operable means comprises a longitudinally extending slot through the wall of said barrel, and a part carried by said slider and extending laterally through said slot and being manually engageably by an operator to move said slider from its second to its first position and vice verse.

5. In the blood sampler of claim 1, wherein the inner end of said barrel opposite said restricted opening is open and of a size to permit the insertion of an evacuated receptacle into said barrel for puncturing of its cover by the second end of said needle after said slider has been moved to its first position.

6. In the blood sampler of claim 5, wherein said slider comprises a cup-shaped member having a bottom wall, and a side wall whose outer diameter is complementary to the inner diameter of said barrel, the inner diameter of said side wall being complementary to the outer diameter of said puncturable cover of said evacuated receptacle, the bottom wall of said cup-shaped member rigidly supporting said needle intermediate its ends, the overall axial length of said slider being less than the axial length of said barrel.

7. In the blood sampler of claim 1, including means for releasibly locking said slider in its first position.

8. In the blood sampler of claim 7, wherein said slider and barrel have interengaging stop means to limit the extension of said needle when said slider is moved to its first position, said releasable locking means being operable to retain said stop means in interengagement after said slider has been moved to its first position and to prevent retraction of said needle and slider as the first end of said needle is inserted into a vein.

9. In a blood sampler of the type comprising a double ended hollow needle having a first end which is adapted to be inserted into a vein and a second end which is adapted to receive thereover a puncturable cover of an evacuated receptacle, the invention comprising a barrel having an inner end and an outer end, a slider slideably received in the barrel and having an open outer end of a size to receive the puncturable cover of an evacuated receptacle when inserted into the open end of said slider past the outer end of said barrel, said slider having an inner end rigidly supporting said double ended needle intermediate its ends and co-axially in said barrel, said barrel having a restricted opening at its inner end through which the first end of said needle extends when said slider is in a first position proximate the inner end of said barrel, said barrel having a length to permit said needle to be entirely withdrawn into said barrel when said slider is moved to a second position remote from the inner end of said barrel, and manually operable means for moving said slider between its first and second positions.

10. In the blood sampler of claim 9, including a cap for closing the restricted opening at the inner end of said barrel.

11. In the blood sampler of claim 9, wherein said inner end of said barrel is tapered and said cap is complementarily tapered for sealing reception over said restricted opening.

12. In the blood sampler of claim 9, including means for releasably locking said slider in its first position.

13. In the blood sampler of claim 12, wherein said manually operable means includes a longitudinally extending slot through the wall of said barrel and a part carried by said slider and extending laterally through said slot for manual engagement by an operator to move said slider between its first and second positions, said releasable locking means comprising a lateral recess in said slot at the end thereof proximate said restricted opening, said laterally extending part on said slider being movable into said lateral recess to releasably lock said needle in its extended position after said slider has been moved to its first position.

* * * * *